(12) United States Patent
Motroni

(10) Patent No.: US 8,308,674 B1
(45) Date of Patent: Nov. 13, 2012

(54) METHODS AND SYSTEMS FOR MULTIFUNCTION NEEDLE/CATHETER DEVICES

(76) Inventor: Mathew Motroni, Chestnut Hill, MA (US)

( * ) Notice: Subject to any disclaimer, the term of this patent is extended or adjusted under 35 U.S.C. 154(b) by 756 days.

(21) Appl. No.: 12/188,594

(22) Filed: Aug. 8, 2008

Related U.S. Application Data

(60) Provisional application No. 60/954,599, filed on Aug. 8, 2007.

(51) Int. Cl.
*A61M 37/00* (2006.01)
(52) U.S. Cl. .................................. 604/6.05; 604/6.16
(58) Field of Classification Search ................ 604/6.16, 604/508, 4.01, 6.01, 6.05
See application file for complete search history.

(56) References Cited

U.S. PATENT DOCUMENTS

| | | | |
|---|---|---|---|
| 1,248,492 A * | 12/1917 | Hill | 604/165.02 |
| 3,055,361 A | 9/1962 | Ballard | |
| 3,662,752 A | 5/1972 | Yokoyama | |
| 4,134,402 A | 1/1979 | Mahurkar | |
| 4,661,094 A * | 4/1987 | Simpson | 604/8 |
| 4,976,703 A | 12/1990 | Franetzki et al. | |
| 5,047,018 A * | 9/1991 | Gay et al. | 604/165.02 |
| 5,195,962 A * | 3/1993 | Martin et al. | 604/43 |
| 5,221,255 A | 6/1993 | Mahurkar et al. | |
| 5,222,949 A | 6/1993 | Kaldany | |
| 5,735,813 A | 4/1998 | Lewis | |
| 5,895,378 A | 4/1999 | Nita | |
| 6,206,849 B1 | 3/2001 | Martin et al. | |
| 6,224,571 B1 | 5/2001 | Bierman | |
| 6,488,662 B2 * | 12/2002 | Sirimanne | 604/164.01 |
| 6,533,763 B1 * | 3/2003 | Schneiter | 604/264 |
| 6,685,664 B2 * | 2/2004 | Levin et al. | 604/5.04 |
| 6,695,832 B2 | 2/2004 | Schon et al. | |
| 6,881,211 B2 | 4/2005 | Schweikert et al. | |
| 2004/0158211 A1 * | 8/2004 | Rogers et al. | 604/284 |

OTHER PUBLICATIONS

Kruse, M. and Khoynezhad, A., "Thoracic endovascular aortic repair (TEVAR) guidewires," CTSNet: The Cardiothoracic Surgery Network, Jul. 27, 2007.
Wikipedia, "Cardiac catheterization," Mar. 16, 2011.
"Apheresis: diagnostic tests and procedures: for patients and families," The Leukemia/Bone Marrow Transplant Program of BC. Retrieved from the Internet URL: http://www.leukemiabmtprograms.org/patients_and_family/procedures. [retrieved Apr. 26, 2011].
"Venous assessment prior to a leukapheresis procedure." Retrieved from the Internet URL: http://www.provenge.com. (2010).
Shandas, R. Cardiovascular Biomechanics, Spring 2004, Univ. of Colo., 1st lecture, pp. 1-14.
Park, J. Y., The Need of Slanted Side Holes for Venous Cannulae, Comput Math Methods Med., vol. 2012, 7 pgs.
Berger, T.M. et al. Potentially Fatal Complications of Peripherally Inserted Central Venous Catheters (PICC's). Swiss Society of Neonatology. Published Oct. 1, 2001, available at http://www.neonet.cen/03_Case_of_the_month/archive/13_miscellaneous_disorders/200.
Orme R. M. L'E et al. Fatal Cardiac Tamponade as a Result of Periphally Inserted Central Venous Catheter: A Case Report and Review of the Literature. Tuesday, Dec. 4, 2007: 2115, available at http://www.rmgh.net/news-room/case-study/398?tmpl=component&print=1&page=.

(Continued)

*Primary Examiner* — Leslie Deak
(74) *Attorney, Agent, or Firm* — Burns & Levinson LLP; Orlando Lopez

(57) ABSTRACT

Multifunction needle/catheter devices and applications. In one instance, the device includes a substantially tubular and flexible catheter, where the catheter has an opening at an end of a distal section of the catheter and one or more apertures longitudinally spaced away from the end of the distal section, and a removable substantially rigid core capable of facilitating vein cannulization, the removable substantially rigid core being disposed within the catheter.

4 Claims, 10 Drawing Sheets

OTHER PUBLICATIONS

Modgil, A. et al. Case Report: The Case of a Missing 55 cm PICC Line. Scientific Medicine, 2009;1(1), pp. 1-3.

Narlawar, R.S. et al. Malpositioned Central Venous Catheter in the Left Renal Vein. Indian J Radiol Imaging 2002; 12:447-8.

Camara, D. Minimizing Risks Associated With Peripherally Inserted Central Catheters in the NICU, MCN Am J Matern Child Nurs. Jan.-Feb. 2001; 26(1):17-21:quiz 22.

Hogan, M.J. Neonatal Vascular Catheters and Their Complications. Radiol Clin North Am. 1999;37(6):1109-25.

Thiagarajan, R.R. et al. Survey of the Use of Peripherally inserted Central Venous Catheters in Children. Pediatrics. Feb. 1997; 99(2):E4.

Joffe, H.V. et al. Upper-Extremity Deep Vein Thrombosis. Circulation, 2002; 106:1874-1880.

Affidavit of Ms. Sharon L. Kohler, RN, MSM, CRNI dated Apr. 16, 2012.

* cited by examiner

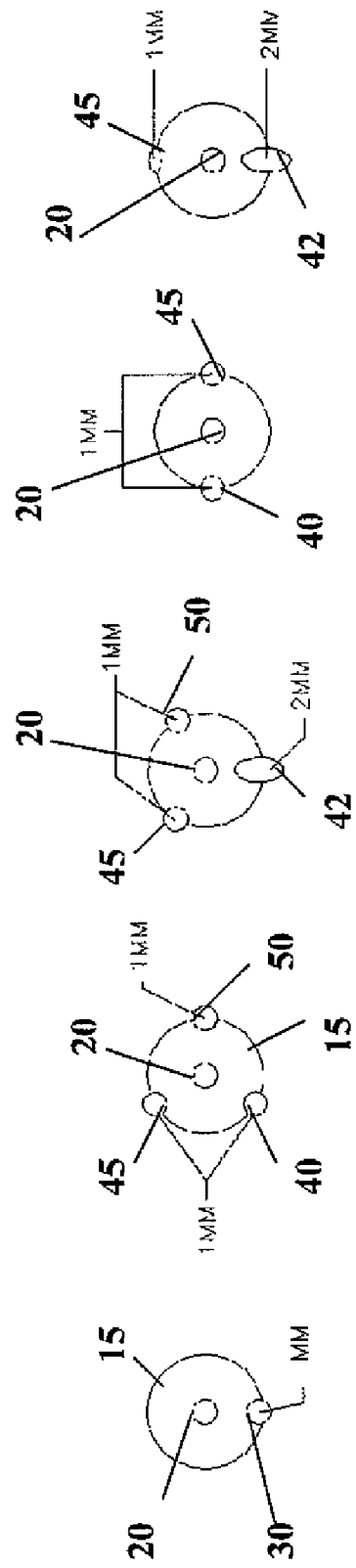

METHODS AND SYSTEMS FOR MULTIFUNCTION NEEDLE/CATHETER DEVICES

CROSS-REFERENCE TO RELATED APPLICATIONS

This application claims priority to U.S. Provisional Patent Application No. 60/954,599, entitled Methods And Systems For Multifunction Needle/Catheter Devices, filed Aug. 8, 2007, the content of which is hereby incorporated by reference in its entirety.

BACKGROUND

These teachings relate generally to needle/catheter devices and, more particularly, to multifunction needle/catheter devices.

Conventional intravenous infusion catheter designs do not permit adequate blood withdrawal (output rates) at volumes that make apheresis treatments possible. Apheresis or fistula needles that are used for apheresis treatments are metal needles that restrict arm mobility and comfort in order to reduce the risk of infiltration. Similarly, donor apheresis component collection is typically performed with metal needles that restrict arm mobility and comfort.

As patients travel from one treatment station to another treatment station a number of venipunctures are required.

Furthermore, Health care is having significant problems dealing with the development of "superbugs" (such as MRSA and VRE) which are forms of bacteria and fungi that have developed from excessive use of antibiotics. These bacteria infect patients and do not respond to normal antibiotic treatments. Many patients require double or triple antibiotic coverage to clear these types of infections. Many of these "superbugs" do not respond to antibiotics at all. If untreated or unsuccessfully treated, the infections become life threatening. Some patients eventually clear the acute aspect of their infection, but then go on to become chronic carriers of these types of organisms.

As many as 100,000 deaths each year are attributed to nosocomial or hospital acquired infections. Some patients arrive to the hospital and they are already infected by these "superbugs." It is possible, in some instances, to acquire exposure to these bacteria in public places (i.e. public transportation, health clubs).

Central lines are prone to infection. Depending on the type of central line, the lines can remain in place for time periods of only a few days to several months. Once the lines are seeded with bacteria it is very difficult to clear the line or patients of infections (they keep infecting one another). The only alternative is to remove the central line, but another central line can not be just reinserted into the patient. The clinician must first clear the patient of any systemic infection or infection from any of these types of "superbugs" otherwise central lines simply become reinfected and the whole process starts all over again. This is a cycle that keeps repeating itself. Many patients cannot recover from surgery or start their chemotherapy treatments as a result. Additionally, many infected central lines if left in place are responsible for causing heart valve infections (remember location of catheter tip in location to heart) that can require months of antibiotics coverage.

Ideally, for many patients it would be best to avoid central line placement all together for the usual reasons (hemorrhage, clot formation and infection).

There is also a need for a needle/catheter that can be used for multiple functions. There is also a need for a needle/catheter that will allow enhanced arm mobility.

BRIEF SUMMARY

In one instance, the apparatus of these teachings includes a substantially tubular and flexible catheter, where the catheter has an opening at an end of a distal section of the catheter and one or more apertures longitudinally spaced away from the end of the distal section, and a removable substantially rigid core capable of facilitating vein cannulization, the removable substantially rigid core being disposed within the catheter.

In one embodiment, the one or more apertures are adapted to allow the removable substantially rigid core to be positioned with respect to the opening and to protrude from the opening.

In one instance, the method of these teachings includes a method for allowing patients to receive multiple treatments via a single venipuncture.

In another instance, the method of these teachings includes a method for providing enhanced patient mobility. When the needle/catheter of these teachings is inserted in place, greater arm flexibility and enhance patient mobility are provided while concurrently reducing risk of infiltration injury.

Other embodiments of the apparatus of these teachings and of the method of these teachings are also disclosed hereinbelow.

For a better understanding of the present teachings, together with other and further needs thereof, reference is made to the accompanying drawings and detailed description and its scope will be pointed out in the appended claims.

BRIEF DESCRIPTION OF THE DRAWINGS

FIGS. 2a-2e are graphical schematic representations of a cross-section of various embodiments of the apparatus of these teachings;

DETAILED DESCRIPTION

Figure 1A:
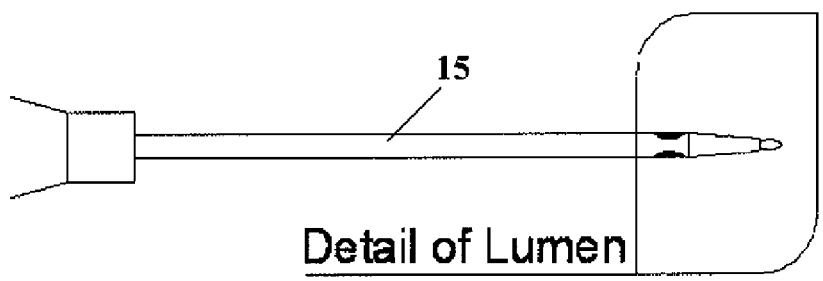
FIGS. 1a-1c are graphical schematic representations of an embodiment of an apparatus of these teachings.
Figure 1B:
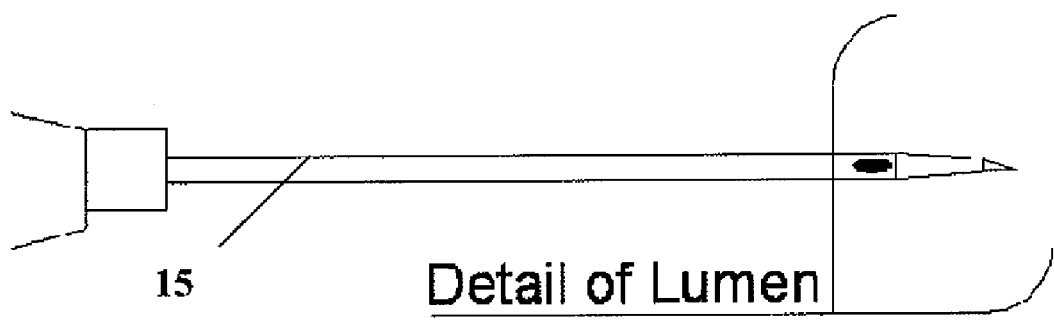
Figure 1C:
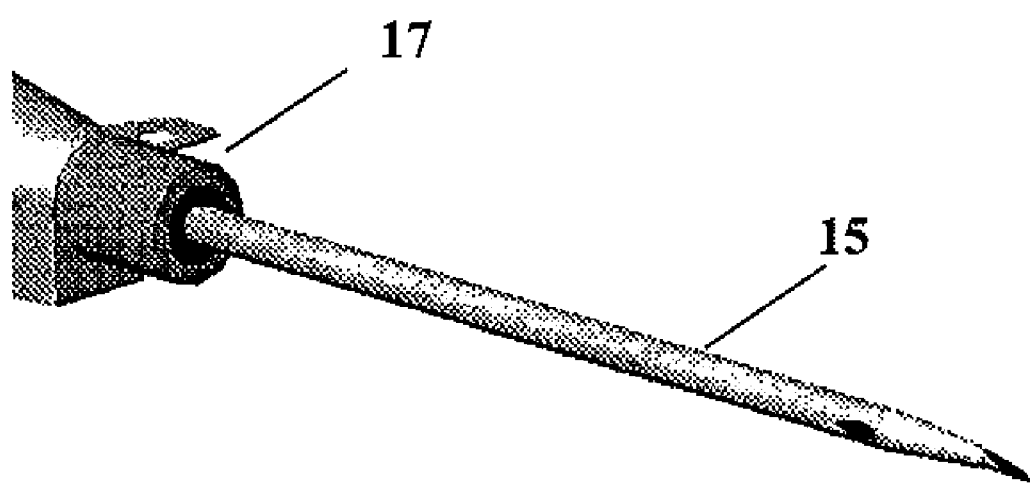
Figure 3A:
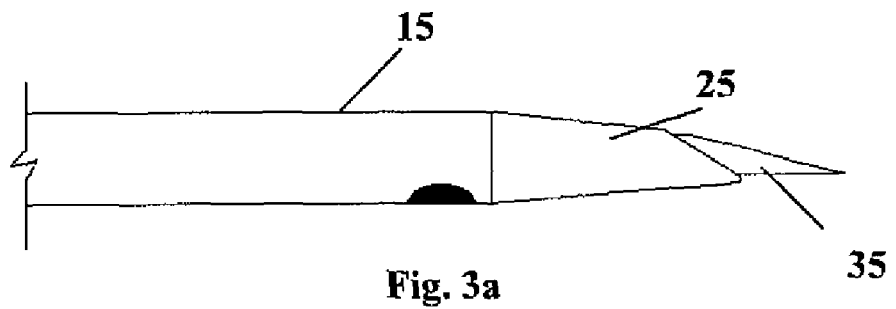
FIGS. 3a-3d are graphical schematic representation of front elevation views of various embodiments of the apparatus of these teachings.
Figure 3B:
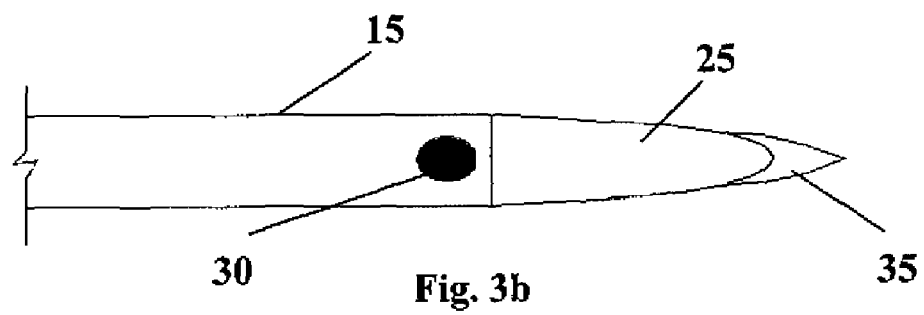
Figure 3C:
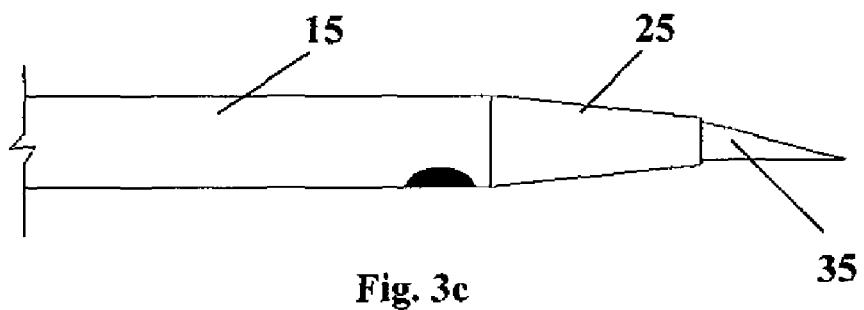
Figure 3D:
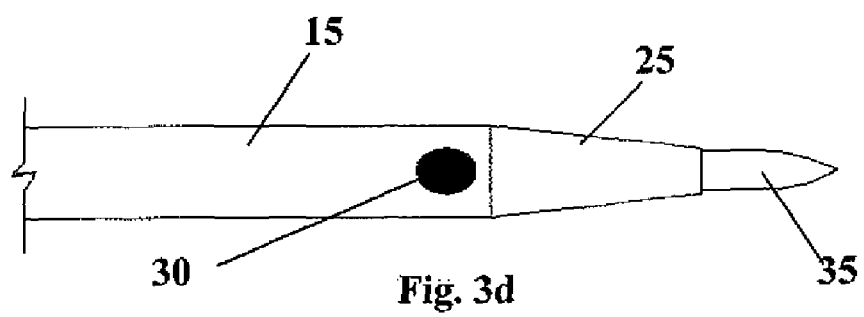
Figure 4:
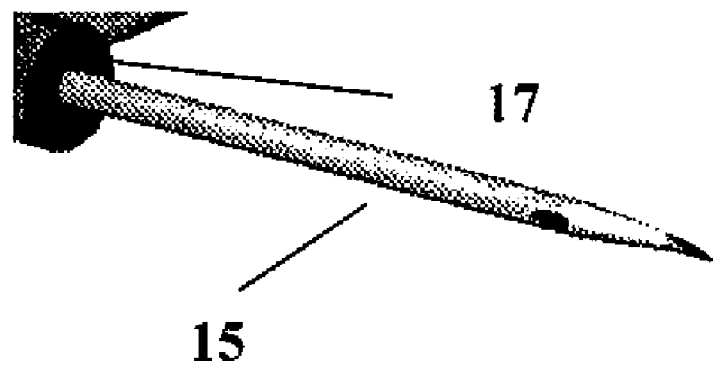
FIG. 4 is graphical schematic representations of another embodiment of the apparatus of these teachings.
Figure 5A:
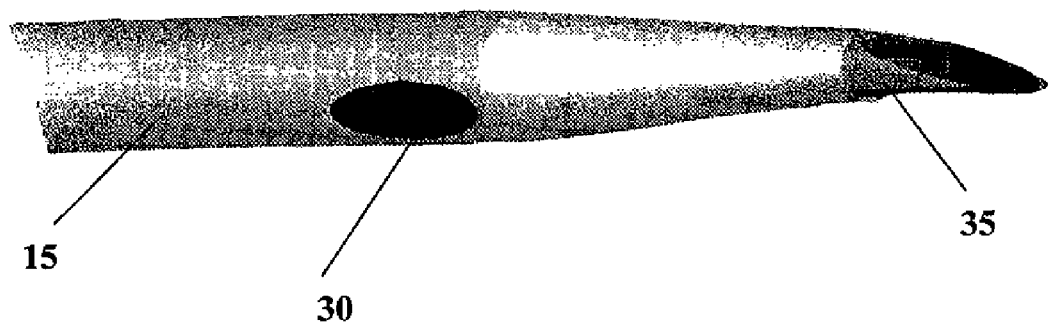
FIGS. 5a-5c are graphical schematic representation of several embodiments of the apparatus of these teachings.
Figure 5B:
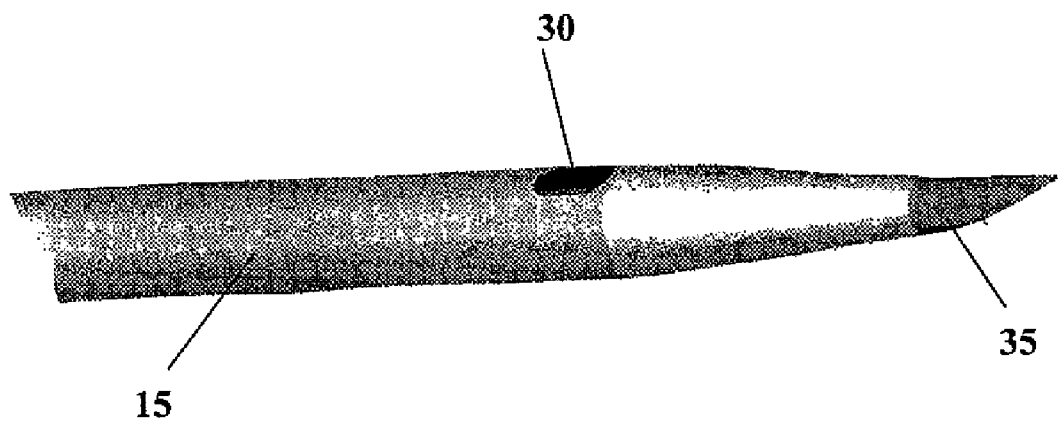
Figure 5C:
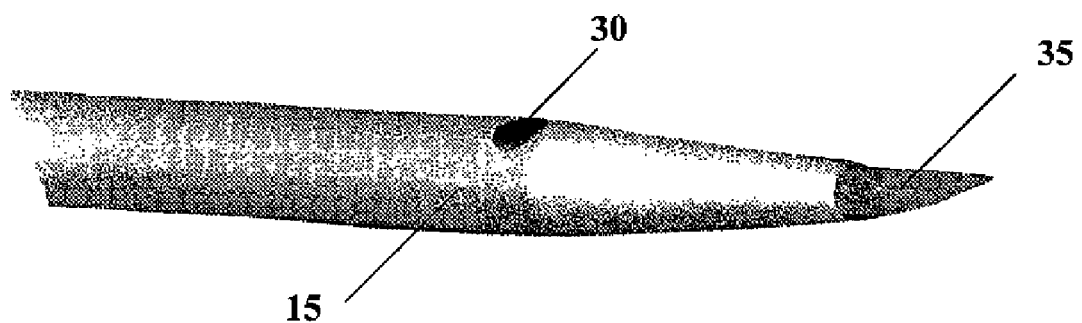
Figure 6:
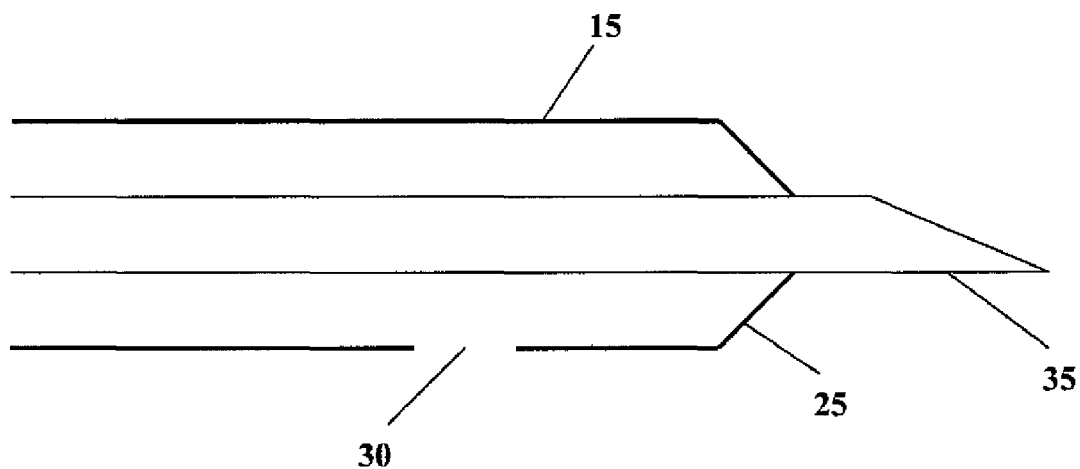
FIG. 6 represents a graphical schematic representation of a cross-sectional view of an embodiment of the apparatus of these teachings.

Referring to FIGS. 1a-6, in one embodiment the apparatus of these teachings includes a substantially tubular and flexible catheter 15, where the catheter has an opening 20 at an end of a distal section 25 of the catheter 15 and one or more apertures 30 longitudinally spaced away from the end of the distal section, and a removable substantially rigid core 35 capable of facilitating vein cannulization, the removable substantially rigid core 35 being disposed within the catheter 15.

FIG. 2a shows a cross-sectional view of an embodiment of the apparatus of these teachings in which the catheter 15 has only one aperture 30. FIGS. 2b, 2c show a cross-sectional view of embodiments of the apparatus of these teachings in which a catheter 15 has three apertures 40, 45 and 50. In the embodiment shown in FIG. 2b, the three apertures 40, 45, 50 are all of the same diameter. In the embodiment shown in FIG. 2c, one aperture 42 has a larger diameter than the other two apertures 45, 50. FIGS. 2d, 2e depict cross-sectional views of embodiments having two apertures 40, 45. In the embodiment shown in FIG. 2d, the two apertures 40, 45, are all of the same diameter. In the embodiment shown in FIG. 2e, one aperture 42 has a larger diameter than the other aperture 45.

In one instance, the catheter 15 of FIGS. 1a-6 comprises a biocompatible material. In another instance, the catheter 15 of FIGS. 1a-6 comprises a radio-opaque material. In one embodiment, the catheter material includes enhanced tear resistant silicone elastomer or polyurethane. In another embodiment, the catheter comprises a silicone tube filled with an x-ray contrast agent or of a polyethylene tube or a composite tube having an inside tube of polyethylene and outside jacket of silicone. In a further embodiment, the catheter is coated with a protective layer 5 of hydrogel, for example, but not limited to, polyethylene glycol. The coating can be, in one instance, produced by immersion of the completely fabricated catheter into the polyethylene glycol.

In yet another instance, the catheter 15, or a section of a catheter 15 is made of a polymer which is inherently quite springy and flexible and biologically compatible such as polyvinylchloride (PVC), polyurethane, silicones, or various block copolymers of polyamides with these polymers or blends or alloys of them. This segment may be doped with radio-opaque materials such as barium sulfate, bismuth trioxide, bismuth subcarbonate, powdered tungsten, powdered tantalum, or the like. It is typical that the catheters 15 or portions of the catheters 15 may include between 10% and 30% by weight of the radio-opaque material, preferably 20-250. In one instance, the range of hardness for the materials of this section can be about Shore 50A to about 75A.

The placement of multiple apertures 30 longitudinally spaced away from the end of the distal section 25 of the catheter 15 creates a flexible peripheral vascular access that permits adequate blood flow withdrawal at outflow rates adequate for apheresis treatments. The placement of multiple apertures 30 can reduce the resistance to inflow of blood into the catheter 15.

In one instance, the catheter is of slightly smaller gauge (for example, but not limited to, about 19 ga), thereby permitting smaller veins to be utilized to complete extracorporeal blood therapies (at slightly lower flow rates). During application, the catheter of slightly smaller gauge being used in smaller veins can avoid the need for central venous access placement and can avoid the associated risks (for example, infectious, mechanical, and thrombotic complications).

The embodiments of the apparatus of these teachings, such as those shown in FIGS. 1a-1c and FIG. 4, can include a fitting for the catheter 15, where the fitting can include a conical or cylindrical receptacle 17 in fluid communication with the catheter 15. In some embodiments, the fitting can also include a pair of lateral wings that extend roughly perpendicularly from a lower portion of the fitting. Each wing can include a through-hole. The fitting can be, in one instance, attached to a medical line securement device (such as, but not limited to, the device disclose in U.S. Pat. No. 6,224,571, which is incorporated by reference herein in its entirety).

In some other embodiments, the fitting also includes a pair of larger lateral wings that extend roughly perpendicularly from a lower portion of the fitting. Each wing can include features that can be utilized to stabilize the wings during use.

Embodiments of the apparatus of these teachings can be utilized to provide enhanced patient mobility during apheresis treatments. Inserting an embodiment of the apparatus of these teachings and removing the substantially rigid core (or stylus), thereby leaving the flexible catheter/needle 15 of these teachings in place enables enhanced patient mobility during aphresis treatments.

Since embodiments of the apparatus of these teachings have properties both of peripheral vascular access needle and of an intravenous infusion catheter, embodiments of the apparatus of these teachings can be utilized to allow patient to receive multiple treatments via a single venipuncture. Inserting an embodiment of the apparatus of these teachings and removing the substantially rigid core (or stylus), thereby leaving the flexible catheter/needle 15 of these teachings in place enables a patient to receive multiple treatments via a single venipuncture since the patient can move from one treatment to another (either physicality or by different treatment stations) and receive a variety of treatments (for example, but not limited to, receiving extracorporeal blood treatment in an apheresis clinic and transferring to a chemo/transfusion clinic and receive blood transfusions or drug infusions) utilizing the same embodiment of the apparatus of these teachings.

Since embodiments of the apparatus of these teachings have properties both of peripheral vascular access needle and of an intravenous infusion catheter, and embodiments of the apparatus of these teachings can be utilized to allow patient to receive multiple treatments via a single venipuncture (embodiments of the apparatus of these teachings can support multipurpose functions), utilizing embodiments of the patterns of these teachings can mitigate the necessity of central line placement (also mitigating the necessity of utilizing peripherally inserted central catheter-PICC-lines). Therefore, utilizing embodiments of apparatus of these teachings may result in a reduced likelihood of vascular catheter associated infections.

Although these teachings has been described with respect to various embodiments, it should be realized these teachings are also capable of a wide variety of further and other embodiments within the spirit and scope of the appended claims.

What is claimed is:

1. A method for providing enhanced patient mobility during apheresis treatments, the method comprising the steps of:

inserting a substantially tubular and substantially flexible catheter, the substantially tubular and substantially flexible catheter having an opening at an end of a distal section of the substantially tubular and flexible catheter and at least one aperture longitudinally spaced away from the end of the distal section of the substantially tubular and flexible catheter, a removable substantially rigid core being disposed within the substantially tubular and substantially flexible catheter; a gauge of the substantially tubular and substantially flexible catheter being selected to enable smaller veins to be utilized to complete extracorporeal blood therapies; said at least one opening being configured to permit adequate blood flow withdrawal necessary to complete apheresis treatments; and removing the substantially rigid core;

providing enhanced patient mobility during apheresis by leaving the substantially tubular and substantially flexible catheter in place.

2. The method of claim 1 wherein the gauge of the substantially tubular and substantially flexible catheter is about 19 ga.

3. A method for allowing patient to receive multiple treatments via a single venipuncture, the method comprising the steps of:

inserting a substantially tubular and substantially flexible catheter, the substantially tubular and substantially flexible catheter having an opening at an end of a distal section of the substantially tubular and flexible catheter and at least one aperture longitudinally spaced away from the end of the distal section of the substantially tubular and flexible catheter, a removable substantially rigid core being disposed within the substantially tubular and substantially flexible catheter, a gauge of the substantially tubular and substantially flexible catheter being selected to enable smaller veins to be utilized to complete extracorporeal blood therapies; said at least one opening being adapted to permit adequate blood flow withdrawal; said at least one opening being configured to permit adequate blood flow withdrawal necessary to complete apheresis treatments; and removing the substantially rigid core; the substantially tubular and substantially flexible catheter being adapted for infusion and adapted for blood removal;

receiving multiple different treatments via the substantially tubular and substantially flexible catheter; the multiple different treatments including apheresis treatments, chemo transfusion treatments, blood transfusions, and drug infusions.

4. The method of claim 3 wherein the gauge of the substantially tubular and substantially flexible catheter is about 19 ga.

* * * * *